United States Patent [19]

Molenaar

[11] Patent Number: 5,635,497

[45] Date of Patent: Jun. 3, 1997

[54] TOPICAL APPLICATION COMPOSITIONS

[75] Inventor: Adrianus P. Molenaar, As Delft, Netherlands

[73] Assignee: Yamanouchi Europe B.V., Leiderdorp, Netherlands

[21] Appl. No.: 414,040

[22] Filed: Mar. 30, 1995

Related U.S. Application Data

[63] Continuation of Ser. No. 128,813, Sep. 29, 1993, abandoned, which is a continuation of Ser. No. 512,959, Apr. 23, 1990, abandoned, which is a continuation of Ser. No. 885,877, Jul. 15, 1986, abandoned, which is a continuation of Ser. No. 583,240, Feb. 24, 1984, abandoned, which is a continuation of Ser. No. 391,451, Jun. 23, 1982, abandoned.

[51] Int. Cl.$^6$ .................................................. A61K 31/56
[52] U.S. Cl. ........................ 514/170; 514/847; 514/937; 514/938
[58] Field of Search ............................. 514/847, 938, 514/170

[56] References Cited

U.S. PATENT DOCUMENTS

| | | | |
|---|---|---|---|
| 2,571,030 | 10/1951 | Govett et al. | 424/68 |
| 2,890,152 | 6/1959 | Babcock et al. | 424/240 |
| 3,210,248 | 10/1965 | Feldman et al. | 424/240 X |
| 3,924,004 | 12/1975 | Chang et al. | 424/240 |
| 3,957,971 | 5/1976 | Oleniacz | 424/240 |
| 4,018,918 | 4/1977 | Ayer et al. | 424/240 |
| 4,048,310 | 9/1977 | Chen et al. | 424/240 |
| 4,124,720 | 11/1978 | Wenmaekers | 424/240 |
| 4,185,100 | 1/1980 | Rovee et al. | 424/240 |
| 4,246,261 | 1/1981 | Van Scott et al. | 424/240 |
| 4,268,499 | 5/1981 | Keil | 424/68 |
| 4,335,104 | 6/1982 | Van Cleave | 424/59 |
| 4,350,605 | 9/1982 | Hughett | 424/68 |

FOREIGN PATENT DOCUMENTS 187103  6/1977  New Zealand .

*Primary Examiner*—Shelley A. Dodson
*Attorney, Agent, or Firm*—McDonnell Boehnen Hulbert & Berghoff

[57] ABSTRACT

A stable topical application composition in the form of a fatty cream comprising 50 to 80% by weight of fatty components, 1.5 to 5% by weight of at least one hydrophilic non-ionic surfactant, a therapeutically effective amount of at least one topically active therapeutic agent and water and a novel method of administering a topically active therapeutic agent.

18 Claims, No Drawings

TOPICAL APPLICATION COMPOSITIONS

This application is a continuation of application Ser. No. 08/128,813, filed Sep. 29, 1993, which is a continuation of Ser. No. 07/512,959 filed Apr. 23, 1990, which is a continuation of Ser. No. 06/885,877, filed Jul. 15, 1986, which is a continuation of Ser. No. 06/583,240 filed Feb. 24, 1984, which in turn is a continuation of Ser. No. 06/391,451, filed Jun. 23, 1982 all of which are now abandoned.

STATE OF THE ART

It is well known that therapeutic agents can be applied to the skin by means of, for example, ointments, creams and lotions and that various skin afflictions can react in different ways to the composition of the vehicle through which the therapeutic agent is administered to the skin. For those afflictions which cause the skin to become dry and flaky, the use of an ointment is generally preferred which generally contains more oil (fatty components) than water although sometimes an ointment contains only fatty constituents. On the other hand, there are skin afflictions in which occlusion of the skin, to avoid drying, is not desirable and in such cases it is better to use a cream containing more water than oil. Ointments have the disadvantage of being sticky and greasy to the touch, and are not easily removed by ordinary washing of the skin or clothing which comes into contact with the ointment. Lotions are generally non-viscous and therefore therapeutic agents contained therein are only in contact with the skin for a relatively short period of time as lotions run off the skin.

To obtain a stable vehicle for ointments containing water and creams, an emulsifying agent or a surfactant is used in their preparation and there are emulsifiers with a lipophilic character to 'dissolve' water in oil, i.e. a W/O emulsifier or wilt a hydrophilic character to 'dissolve' oil in water, i.e. an O/W emulsifier. In the case of an ointment which contains more oil than water, usually a W/O emulsifier is used and the ointment consists of a continuous oil phase in which small water particles are present. In the case of a cream which contains more water than oil, an O/W emulsifier is used and the cream consists of a continuous water phase in which small oil particles are present. To determine if a formulation is an ointment or a cream, colored compounds can be used which dissolve either in the oil-phase or the water-phase, and a distinction can be made with a microscope.

OBJECTS OF THE INVENTION

It is an object of the invention to provide a novel stable topical application composition in the form of a fatty cream containing more fatty components than water with oil-in-water non-ionic emulsifier.

It is another object of the invention to provide a novel method of applying therapeutic agents topically.

These and other objects and advantages of the invention will become obvious from the following detailed description.

THE INVENTION

The novel stable topical application of the invention is in the form of a fatty cream comprising 50 to 80% by weight of fatty components, 1.5 to 5% by weight of at least one hydrophilic non-ionic surfactant, a therapeutically effective amount of at least one topically active therapeutic agent and water. The compositions surprisingly has been found to be stable even though an oil-in-water non-ionic surfactant with a hydrophilic character is used. The composition preferably contain 60 to 70% by weight of fatty material.

The 'fatty-creams' of the invention may be prepared by the use of conventional methods for the manufacture of ointments and creams and microscopic examination of the creams sometimes shows a picture of a complex emulsion, and sometimes an oil-in-water emulsion depending on the intensity of the mixing procedure. In the case of a complex emulsion, the continuous phase is the oily components in some parts of the emulsion and in other parts the continuous phase is water. The fatty-creams have an occlusive action when applied to skin due to the high oil content and the skin becomes moist and therefore there is better penetration by the therapeutic agent employed therein. Moreover the fatty creams, in contrast with ointments, are non-greasy and are readily removeable from the skin or other materials which come into contact with the creams.

The fatty materials which are incorporated in the fatty-creams of the invention are those commonly used in the preparation of ointments and creams and preferably, a mixture of fatty compounds which may be solid, semi-solid and/or liquid at ambient temperature is used in the preparation of the fatty-creams. The fatty compounds may be, for example, waxes e.g. white soft paraffin, liquid paraffin, fatty alcohols and esters e.g. cetyl/stearyl alcohol, myristyl alcohol and glycerin monostearate, vegetable oils e.g. cottonseed, coconut, soybean or peanut oil, mineral oils or liquid silicones. Preferably, a combination of cetyl/stearyl alcohol, liquid paraffin and white soft paraffin is employed.

The amount of hydrophilic non-ionic surfactant which may be liquid or solid used in the preparation of the fatty-creams of the invention is preferably from 1.5 to 3.5%, more preferably 3%, by weight of the final composition. The surfactant or emulsifier should preferably have a high HLB or Hydrophilic-Lipophile Balance number as described by Balsam et al [Cosmetics, Science and Technology, Vol. III, pages 583–596] and advantageously, the HLB number should be 14 or greater. The surfactant is preferably cetomacrogol 1000 (i.e. polyethylene glycol (1000) monocetyl ether) but other surfactants which may be used are polysorbate 60 (i.e. polyoxyethylene (20) sorbitan monostearate), and polysorbate 80 or Tween 80 (i.e. polyoxyethylene (20)sorbitan monooleate). Advantageously, only one surfactant is employed.

The amount of water, which is preferably de-ionised, used in the preparation of the fatty-creams of the invention may range from 20% to 35% by weight of the final composition and advantageously about 30% of water is used.

The topically-active thereapeutic agent(s) incorporated in the fatty creams of the invention may be a steroid such as an anti-inflammatory steroid, an antibiotic or a chemotherapeutic agent, or a combination of such therapeutically useful agents. Examples of therapeutic agent are hydrocortisone-17α-butyrate, hydrocortisone, triamcinolone acetonide, salicylic acid and derivatives thereof, tar products, sulfur compounds, iodine compounds, nicotinic acid and derivatives thereof, hexachlorophene or retinoic acid. The amount of therapeutic agent which may be soluble in the aqueous- or oil-phase of the fatty-creams will be that suitable for the application intended.

When the therapeutic agent such as hydrocortisone-17α-butyrate is soluble in the aqueous phase of the fatty cream, a better activity can be obtained than in a normal cream or ointment as the therapeutic agent is dissolved in a smaller volume of water, leading to a higher concentration of the therapeutic agent.

It is useful to include in the fatty-creams of the invention a buffering agent to maintain a desired pH value and the buffering agent may be, for example, a combination of (i) citric acid and sodium citrate, (ii) phosphoric acid and sodium phosphate, or (iii) lactic acid and sodium lactate, as appropriate for the desired pH. Where the therapeutic agent is hydrocortisone-17α-butyrate, a slightly acidic environment of about pH 3.5 to 4.5 is needed to prevent hydrolysis of the butyrate and a combination of citric acid and sodium citrate is particularly useful for this purpose.

The fatty-creams of the invention may also contain—as is common practice in ointments and creams—a preservative to prevent, for example, bacterial attack. Suitable preservatives are methyl hydroxybenzoate, chlorocresol, sorbic acid and benzoic acid.

As mentioned above, the fatty-creams of the invention may be prepared by conventional means, but a preferred method involves mixing the 'fatty' components e.g. cetyl/stearyl alcohol, liquid paraffin and white soft paraffin with the hydrophilic non-ionic surfactant preferably cetomacrogol 1000, and heating the mixture at, for example, 70°–80° C. Water (preferably de-ionised), buffering agent and preservative are mixed separately in a suitable ointment-mixer and heated e.g. at 70°–80° C. until a solution is obtained. A small portion of the resulting solution is separated and cooled to ambient temperature, and then the therapeutic agent is added to it. The liquid fatty composition at elevated temperature of about 70°–80° C. is added to the larger portion of the aqueous solution and then, after vigorous stirring under reduced pressure to avoid air bubbles in the final fatty-cream, the aqueous solution or suspension containing the therapeutic agent is added to it at normal pressure. After vigorously mixing the mass at about ambient temperature for an appropriate length of time—once again under reduced pressure—, a fatty-cream is obtained.

The temperature of the final mixing of the components of the fatty-cream and the agitation involved can affect the form of the emulsion (oil-in-water and/or water-in-oil) obtained. Preferably, it is effected at 20°–25° C. with vigorous agitation.

The fatty-creams of the invention obtained preferably comprise 'oil' globules with a mean diameter of 1–2 μm with a maximum of 5 μm and as a result of the high fat-content, an aqueous phase is usually hardly perceptible. Possibly the water is attached as a thin film to the surface of the globules, still forming the continuous phase. The fatty smooth creams of the present invention are extremely stable under normal conditions, especially when they are emulsions containing mostly oil particles of very small mean diameter, e.g. 1–2 μm.

The present invention also includes within its scope fatty-creams as hereinbefore described which do not contain one or more topically-active therapeutic agents, and also the preparation of such topical cream bases.

The novel method of the invention of topically applying a therapeutic agent to a warm-blooded animal comprises applying to the skin of a warm-blooded animal a composition in the form of a fatty cream comprising 50 to 80% by weight of fatty components, 1.5 to 5% by weight of at least one hydrophilic non-ionic surfactant, a therapeutically effective amount of at least one topically active therapeutic agent and water.

In the following examples there are described several preferred embodiments to illustrate the invention. However, it is to be understood that the invention is not intended to be limited to the specific embodiments.

EXAMPLE 1

3000 g of cetyl/stearyl alcohol, 1500 g of cetomacrogol 1000, 9000 g of liquid paraffin and 21000 g of white soft paraffin were mixed together and heated to 70°–80° C.

60 g of sodium citrate, 90 g of citric acid and 100 g of methyl hydroxybenzoate were added to 15500 g of de-ionished water in a suitable ointment-mixer such as a 50 kg Unimix, manuf. Heagen and Rinau, Bremen, West-Germany. While stirring, the mixture was heated to 70°–80° C. and kept at this temperature until the compounds were dissolved and 2000 g of the resulting solution were separated and cooled to room temperature.

The prepared liquid fatty composition was added at a temperature of 70°–80° C. to the remaining solution and after vigorous mixing under a reduced pressure of 50 mm Hg, the mass was gradually cooled to 20°–25° C. 50 g of hydrocortisone-17α-butyrate were uniformly suspended in the separated portion of the aqueous solution using an Ultra-Turrax mixer, manuf. Janke and Kunkel, West Germany and after releasing the vacuum in the ointment mixer using filtered air, the suspension containing hydrocortisone-17α-butyrate was added to the cream. After closing of the mixer and vigorous mixing of the contents under a reduced pressure of 50 mm Hg for at least half an hour, the cream was homogenized. After releasing the vacuum, the 50 kg of fatty-cream were transferred into a container from which it could be filled into tubes and jars. The 50 kg of fatty-cream on examination under a microscope comprised oil-globules with a mean diameter of 1–2 μm, the larger ones being up to 5 μm.

EXAMPLE 2

The procedure of Example 1 was repeated to obtain a fatty-cream but replacing the 50 g of hydrocortisone-17α-butyrate with 500 g of hydrocortisone and using 15050 g of de-ionised water instead of 15500 g.

EXAMPLE 3

The procedure of Example 1 was repeated to obtain a fatty-cream but replacing the 50 g of hydrocortisone-17α-butyrate with 50 g of triamcinolone acetonide.

EXAMPLE 4

The procedure of Example 1 was repeated except that the hydrocortisone-17α-butyrate (viz. the therapeutic agent) was omitted and therefore the step of separation of 2000 g of the prepared aqueous solution was not effected to obtain a fatty-cream base which could be used as a pharmaceutical or therapeutical base.

EXAMPLES 5 TO 8

The procedures of Examples 1 to 4 were repeated with replacement of the cetyl/stearyl alcohol with glyceryl monostearate.

EXAMPLES 9 TO 12

The procedures of Examples 1 to 4 were repeated with replacement of the cetomacrogol 1000 with polysorbate 80.

EXAMPLES 13 TO 16

The procedures of Examples 1 to 4 were repeated with replacement of the liquid paraffin with a vegetable oil selected from cottonseed, refined coconut and soybean oils.

EXAMPLES 17 TO 20

The procedures of Examples 1 to 4 were repeated with replacement of part or all the white soft paraffin with a corresponding amount of hardened peanut oil.

EXAMPLES 21 TO 24

The procedures of Examples 1 to 4 were repeated with replacement of the citric acid and sodium citrate with other buffering systems, viz. phosphoric acid and sodium phosphate with modification of the ratio of both to give the desired pH.

EXAMPLES 25 TO 28

The procedures of Examples 1 to 4 were repeated except that no buffering agent was added.

EXAMPLES 29 TO 32

The procedures of Examples 1 to 4 were repeated with the methyl hydroxybenzoate being replaced by another preservative selected from chlorocresol, sorbic acid and benzoic acid.

All the products of Examples 5 to 32 were fatty-creams similar to that obtained in Example 1.

Various modifications of the compositions and methods of the invention may be made without departing from the spirit or scope thereof and it is to be understood that the invention is to be limited only as defined in the appended claims.

What is claimed is:

1. An oil-in-water, fatty cream composition for topical administration comprising from 60 to 80 percent by weight of fatty components, from 1.5 to 5 percent by weight of at least one non-ionic, hydrophilic surfactant having an HLB of at least 14, about 6% of fatty alcohols and esters, a therapeutically effective amount of at least one topically active therapeutic agent, and water, provided the topically active therapeutic agent is not dithranol or its derivatives.

2. An oil-in-water, fatty cream composition for topical administration comprising from 60 to 80 percent by weight of fatty components, from 1.5 to 5 percent by weight of at least one non-ionic, hydrophilic surfactant having an HLB of at least 14, about 6% of fatty alcohols and esters, and water, provided the composition does not contain a therapeutically effective amount of dithranol or its derivatives.

3. A composition of claim 1 wherein the amount of fatty composition is 60% to 70% by weight of the composition.

4. A composition of claim 1 wherein the fatty materials included in the composition are a mixture of cetyl/stearyl alcohol, liquid paraffin and white soft paraffin.

5. A composition of claim 1 wherein the amount of surfactant is from 1.5 to 3.5% by weight of the composition.

6. A composition of claim 1 wherein the hydrophilic nonionic surfactant is cetomacrogrol 1000.

7. A composition of claim 1 wherein the amount of water present is from 20% to 35% by weight of the composition.

8. A composition of claim 7 wherein the amount of water is about 30% by weight.

9. A composition of claim 1 wherein the therapeutic agent is an anti-inflammatory steroid.

10. A composition of claim 9 in which the steroid is hydrocortisone-17α-butyrate.

11. A composition of claim 1 containing a buffering agent to maintain a desired pH value in the composition.

12. A composition of claim 11 wherein the buffering agent is a combination of citric acid and sodium citrate.

13. A composition of claim 11 which contains a preservative.

14. A method of topically administering a therapeutic agent to a warm-blooded animal comprising applying to the skin of a warm-blooded animal a composition of claim 1.

15. The method of claim 14 wherein the amount of fatty component is 60 to 70% by weight of the composition.

16. The method of claim 14 wherein the fatty component is a mixture of cetyl alcohol, stearyl alcohol, liquid paraffin and white soft paraffin.

17. The method of claim 14 wherein the therapeutic agent is an anti-flammatory steroid.

18. The method of claim 17 wherein the steroid is hydrocortisone-17α-butyrate.

* * * * *